(12) United States Patent
Nunes et al.

(10) Patent No.: US 10,282,838 B2
(45) Date of Patent: May 7, 2019

(54) IMAGE ANALYSIS FOR ASSESSING IMAGE DATA

(71) Applicant: General Electric Company, Schenectady, NY (US)

(72) Inventors: Camila Patricia Bazilio Nunes, Rio de Janeiro (BR); Marina Lundgren de Almeida Magalhaes, Rio de Janeiro (BR); Marcelo Blois Ribeiro, Rio de Janeiro (BR); Dario Augusto Borges Oliveira, Sao Paulo (BR); Eudemberg Fonseca Silva, Rio de Janeiro (BR); Felipe Santos De Andrade, Rio de Janeiro (BR); Marco Blumenthal, Jena (DE); Giovanni John Jacques Palma, Issy les Moulineaux (FR); Serge Louis Wilfrid Mueller, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 72 days.

(21) Appl. No.: 15/401,884

(22) Filed: Jan. 9, 2017

(65) Prior Publication Data
US 2018/0197288 A1    Jul. 12, 2018

(51) Int. Cl.
*G06T 3/00* (2006.01)
*G06T 7/00* (2017.01)
(Continued)

(52) U.S. Cl.
CPC .......... *G06T 7/0012* (2013.01); *A61B 6/4405* (2013.01); *A61B 6/502* (2013.01);
(Continued)

(58) Field of Classification Search
CPC .. A61B 5/05; A61B 8/485; A61B 8/14; A61B 8/406; A61B 5/015; A61B 6/025;
(Continued)

(56) References Cited

U.S. PATENT DOCUMENTS

| 5,803,082 | A | * | 9/1998 | Stapleton | ............. | A61B 5/0091 600/407 |
| 5,907,406 | A | * | 5/1999 | Papaioannou | ....... | A61B 5/0091 356/432 |

(Continued)

FOREIGN PATENT DOCUMENTS

WO    20160057960 A1    4/2016

OTHER PUBLICATIONS

Doi, Kunio; "Computer-aided diagnosis in medical imaging: Historical review, current status and future potential", computerized Medical Imaging and Graphics, vol. 31, Issues 4-5, pp. 198-211, Mar. 8, 2007.

(Continued)

*Primary Examiner* — Aklilu K Woldemariam

(57) ABSTRACT

The present approach relates to providing image quality feedback to personnel (e.g., a technician) acquiring non-invasive images in real-time or near real-time. By way of example, the proposed approach may automatically assess the quality of images in real-time by evaluating the images for the presence or absence of non-conformities using processor-implemented, rule-based algorithms running partly or completely in parallel to one another. The proposed approach improves the image analysis pipeline by efficiently providing notification of and/or discarding low-quality or unsuitable images or exams after they are taken, such as in within seconds or minutes.

15 Claims, 11 Drawing Sheets

(51) Int. Cl.
*G06F 19/00* (2018.01)
*A61B 6/00* (2006.01)
*G01T 7/00* (2006.01)

(52) U.S. Cl.
CPC ............ *A61B 6/5258* (2013.01); *A61B 6/563* (2013.01); *A61B 6/586* (2013.01); *G01T 7/00* (2013.01); *G06F 19/321* (2013.01); *G06T 2207/10116* (2013.01); *G06T 2207/30068* (2013.01)

(58) Field of Classification Search
CPC ........... A61B 6/035; A61B 6/14; A61B 6/466; A61B 6/484; A61B 6/547; A61B 6/583; A61B 6/469; A61B 6/502; A61B 6/505; A61B 6/548; A61B 34/20; A61B 90/06; A61B 8/082; A61B 2562/0238; A61B 5/0091; A61B 5/4312; A61B 5/7285; A61B 5/0507; A61B 5/7257; A61B 8/0825; A61B 8/15; A61B 8/4209; A61B 8/4483; A61B 5/0064; A61B 5/0073; A61B 6/0457; A61B 6/4021; A61B 6/4494; A61B 2034/102; A61B 2034/108; A61B 17/154; A61B 17/155; A61B 17/157; A61B 17/158; A61B 17/1666; A61B 17/1668; A61B 17/1675; A61B 17/1739; A61B 17/1746; A61B 17/176; A61B 5/415; A61B 5/418; A61B 6/0414; A61B 6/4417; A61B 8/4281; A61B 8/4416; A61B 2034/105; A61B 2034/2063; A61B 2034/2065; A61B 2090/363; A61B 2090/367; A61B 34/10; A61B 6/5217; A61B 6/563; Y10S 128/922; G06T 11/006; G06T 7/0012; G06T 2207/30068; G06T 2207/30004; G06T 2207/30196; G06T 7/44; G06T 7/73; C12C 1/6841; C12C 1/6883; G01J 2003/2866; G01J 3/02; G01J 3/12; G01J 3/1256; G01J 3/26; G01J 3/2823; G01J 3/4406; G01J 3/453; G01N 1/30; G01N 2021/6423; G01N 2021/6441; G01N 21/6428; G06F 19/321; G06F 17/30247; G06F 19/328; G06F 9/5072; C12Q 1/6841; C12Q 1/6883; G06Q 50/02; G16H 15/00
USPC ....... 382/128, 131, 132, 276, 155, 157, 168, 382/170, 181, 203, 224, 260
See application file for complete search history.

(56) References Cited

U.S. PATENT DOCUMENTS

| | | | |
|---|---|---|---|
| 6,023,341 A * | 2/2000 | Colak | A61B 5/0091 |
| | | | 356/435 |
| 7,146,031 B1 * | 12/2006 | Hartman | G06T 7/0012 |
| | | | 382/132 |
| 7,672,491 B2 | 3/2010 | Krishnan et al. | |
| 8,553,965 B2 * | 10/2013 | Zhao | G06F 9/5072 |
| | | | 382/131 |
| 9,008,382 B2 | 4/2015 | Highnam et al. | |
| 9,314,196 B2 * | 4/2016 | Pryor | A61B 5/0031 |
| 9,355,450 B2 | 5/2016 | Pearson | |
| 9,430,828 B2 | 8/2016 | Wu et al. | |
| 9,949,719 B2 * | 4/2018 | Zhang | A61B 8/4416 |
| 2003/0086523 A1 * | 5/2003 | Tashiro | A61B 6/00 |
| | | | 378/19 |
| 2004/0161075 A1 * | 8/2004 | Amitani | A61B 6/0457 |
| | | | 378/37 |
| 2006/0258929 A1 * | 11/2006 | Goode, Jr. | A61B 5/0031 |
| | | | 600/345 |
| 2006/0287596 A1 * | 12/2006 | Johnson | A61B 5/4312 |
| | | | 600/437 |
| 2007/0248210 A1 | 10/2007 | Selse et al. | |
| 2007/0276256 A1 * | 11/2007 | Iddan | A61B 5/0091 |
| | | | 600/473 |
| 2008/0037852 A1 | 2/2008 | Zhou et al. | |
| 2008/0243127 A1 * | 10/2008 | Lang | A61B 5/4528 |
| | | | 606/87 |
| 2010/0111395 A1 * | 5/2010 | Tannakoshi | A61B 6/469 |
| | | | 382/132 |
| 2011/0206249 A1 | 8/2011 | Mathew | |
| 2012/0041785 A1 * | 2/2012 | Tsunonnori | A61B 6/5235 |
| | | | 705/3 |
| 2013/0150700 A1 | 6/2013 | Kälvesten et al. | |
| 2015/0305696 A1 * | 10/2015 | Yamakawa | A61B 6/14 |
| | | | 378/19 |
| 2016/0171682 A1 | 6/2016 | Abedini et al. | |
| 2018/0055644 A1 * | 3/2018 | Mahfouz | A61B 34/20 |

OTHER PUBLICATIONS

Nishikawa, Robert M.; "Current status and future directions of computer-aided diagnosis in mammography", Computerized Medical Imaging and Graphics, vol. 31, Issues 4-5, pp. 224-235, Jun.-Jul. 2007.

Eadiea, Leila H., et al.; "A systematic review of computer-assisted diagnosis in diagnostic cancer imaging", European Journal of Radiology, vol. 81, Issue: 1, pp. e70-e76, Jan. 2012.

"Pattern: Microservice Architecture," Microservice Architecture, Retrieved from the Internet URL: http://www.definiens.com/solutions-overview/, pp. 1-6 (Aug. 30, 2018).

"Visual Recognition," IBM, Retrieved from the Internet URL: https://www.ibm.com/smarterplanet/us/en/ibmwatson/developercloud/visual-recognition.html , pp. 1-6 (Aug. 30, 2018).

Bhavani, S.R., et al., "CIMIDx: Prototype for a Cloud-Based System to Support Intelligent Medical Image Diagnosis With Efficiency," JMIR Medical Informatics, vol. 3, Issue. 1, pp. 1-23 (Mar. 27, 2015).

Mulimani V., and Kulkarni, D.A., "A Proposed model for the Implementation of Cloud based Decision Support System for Diagnosis of Breast Cancer using Digital Mammograms," International Journal of Latest Trends in Engineering and Technology, vol. 5, Issue. 3, pp. 276-281 (May 2015).

Ojog, I et al., "A Cloud Scalable Platform for DICOM Image Analysis as a Tool for Remote Medical Support," eTELEMED 2013 : The Fifth International Conference on eHealth, Telemedicine, and Social Medicine, pp. 246-249 (2013).

Shaulsky, G. et al., "Data Mining Fruitful and Fun", Retrieved from the Internet URL: http://orange.biolab.si/, pp. 1-8 (Aug. 30, 2018).

Extended European Search Report issued in connection with corresponding EP Application No. 18150462.2 dated Jun. 7, 2018.

* cited by examiner

US 10,282,838 B2

IMAGE ANALYSIS FOR ASSESSING IMAGE DATA

BACKGROUND

The subject matter disclosed herein relates to image analysis approaches suitable for use in a distributed, remote, or mobile imaging context where real-time or near real-time image quality assessment using consistent or uniform standards is useful.

In various modern contexts, non-invasively acquired images are used for identifying or localizing features in a subject or object that would otherwise not be evident from external examination alone. By way of example, in healthcare facilities, non-invasive imaging approaches are used for identifying, localizing, and/or diagnosing aberrant or diseased tissues, structural abnormalities or irregularities, foreign objects within the body, and so forth. Conversely, in security screening contexts, non-invasive imaging approaches may be used to identify objects or items deemed of interest in a security context, such as contraband or prohibited items within a package or bag or present in a person's clothing.

By way of an illustrative medical example, one purpose to which such techniques are applied is the acquisition of mammographic images for use in identifying and diagnosing a clinically relevant medical condition. Such images of breast tissue may be acquired so as to identify or diagnose lesions or irregularities in the breast tissue. Based upon this information, patient may then be treated or cleared as appropriate from the image data.

One situation that may arise is that the prevalence and/or mobility of such imaging systems exceed availability of skilled personnel to facilitate acquisition of quality images. For example, in the context of mammography, mobile or portable systems may sometimes be employed to provide screening opportunities in remote or rural settings or in other non-clinical settings (i.e., outside the hospital or clinic). In such scenarios, the personnel involved may be less experienced in acquiring quality images or may be skilled but, due to the setting and circumstances may have difficulty in acquiring quality images in a time frame that is available and/or with the equipment that is available. In such contexts the technician also may be unskilled or inexperienced at reading the acquired images and thus may not be capable of promptly determining whether an acquired image or images is of suitable quality or otherwise meets clinical standards. As a consequence, a set of images acquired for a given patient may be determined to be unsuitable or otherwise of insufficient quality after the patient has been moved from a given clinical pose, or in some circumstances after the patient has already left the screening site. Such scenarios result in a missed diagnostic opportunity or in the patient having to return to be reimaged. As will be appreciated, though a mammography example is described above, similar situation s may arise in other medical imaging contexts and/or in non-medical contexts, including security screening contexts.

BRIEF DESCRIPTION

In one embodiment, an imaging system is provided. In accordance with this embodiment, the imaging system includes data acquisition circuitry configured to generate one or more images that are transmitted directly or indirectly to a remote processing resource configured to execute a plurality of services which each evaluate the one or more images for a different type of non-conformity. The imaging system also includes an operator interface and display configured to execute an application that displays identified non-conformities of the one or more images identified by the remote processing resource.

In a further embodiment, an image analysis architecture is provided. In accordance with this embodiment, the image analysis architecture includes an application interface configured to be displayed at the site of an imaging system and to facilitate the transfer of one or more image files to a remote processing resource. The image analysis architecture also includes a plurality of services executable on the remote processing resource. At least a portion of the services are configured to execute in parallel. Each service is configured to analyze the one or more image files for a respective type of non-conformity and to provide a notification of any identified non-conformities via the application interface.

In an additional embodiment, a method for remotely assessing image quality is provided. In accordance with this method an image of a patient or object generated at a site of an imaging system is received. The image is processed using a plurality of image quality analysis services, at least a portion of which execute in parallel. The image quality service analytics are executed on a network-based architecture physical remote form the site of the imaging system. One or more notifications of non-conformities identified by the image quality analysis services are transmitted to the site of the imaging system in less than a minute from the time the image was acquired.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
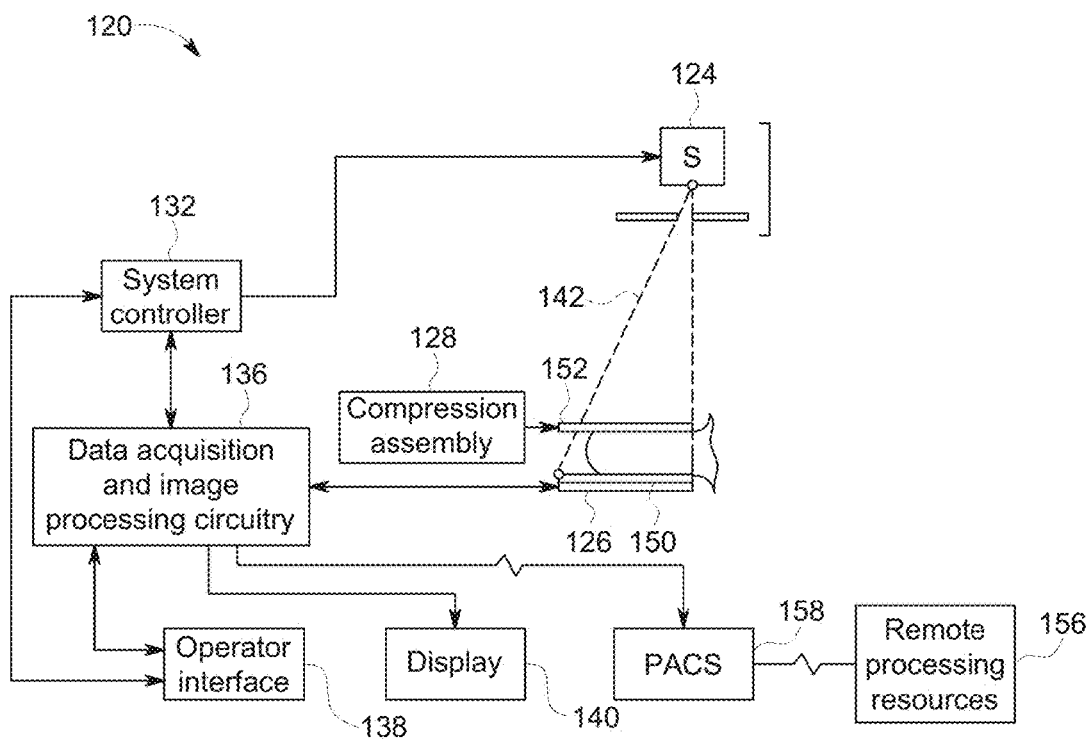
FIG. 1 is a block diagram of a mammography system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure While the following discussion and examples are generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

The present approach facilitates automatically providing image quality feedback to personnel (e.g., a technician) acquiring non-invasive images in real-time or near real-time, such as in less than 5 seconds, 10 seconds, 20 seconds, 30 seconds, 1 minute, 2 minutes, or 5 minutes of the image being acquired. By way of example, the proposed approach may automatically assess the quality of mammography images in real-time by evaluating the images for the presence or absence of non-conformities using processor-implemented, rule-based algorithms running partly or completely in parallel to one another. As used herein a non-conformity in the imaging or image quality context may be understood to occur when an image does not conform to an established or expected image quality or clinical standard. Thus, non-conformities may be related to an identifiable image irregularity that may arise due to system or hardware issues, incorrect use of the equipment, examination specific occurrences or irregularities, and/or failure to conform to a clinical standard or expectation. In instances where the non-conformity is related to an image failing to meet a clinical expectation or standard, such non-conformities may be due to the imaged tissue not being at a prescribed orientation or location, such as due to bad positioning of the tissue or object being imaged.

The proposed approach improves the image analysis pipeline by efficiently providing notification of and/or discarding low-quality or clinically unsuitable images or exams after they are taken, such as in within seconds or minutes. Such notification may, in certain implementations occur while patient or object is still present and/or positioned for a follow-up imaging attempt. This is in contrast to situations where an indication of poor image quality or diagnostic insufficiency may be provided after the patient has dressed and left the examination area or facility or after the object being screened has passed through the screening area. In this manner, the patient or object may be re-imaged with minimal disruption.

In accordance with the present disclosure the image analysis approach may be implemented as a cloud-based image analysis instance (or other remote or networked implementation) so as to provide real-time or near real-time feedback to personnel tasked with acquiring the image data regardless of geographic location. Such approaches may be used in both diagnostic clinical settings (or other fixed or dedicated imaging sites) as well as in remote or mobile imaging solutions (such as mammography screening trucks that travel from region to region to provide mammography services). In this manner, a remote or mobile site has access to the image quality assessment in real-time. One further benefit to such approaches is that, in remote or mobile imaging contexts, the remotely acquired images are analyzed using the same standards as images acquired in a more traditional clinical environment. A further benefit, which may be appreciated from the discussion below, is the straightforward scalability of processes in a cloud-based architecture or comparable networked architecture, which provides the ability to grow the equipment and services as needed to allow computational process scaling in imaging contexts. Such cloud- or network-based approaches also essentially unlimited computational processing capability without the need of local infra-structure, as may be suitable for remote and/or portable imaging contexts.

To the extent used herein, references to cloud-based computing or processing should be understood to relate to network-based computing approaches (e.g., internet-based) which rely on shared processing resources on demand to systems having a connection to the network in question, such as image acquisition or processing systems in the present context. In this manner, the processing resources in questions may be made available in a manner not limited by geography or distance to provide similar or comparable experiences and resources to those systems able to access the network in question. Computing resources that may be made available and shared in this manner include, but are not limited to, computer networks, application and/or service servers, web servers, databases and other data stores, licensing servers, and so forth. Such cloud- or network-based services may be housed on or in a data center owned and operated by a third-party or by a party providing a service or application having a defined relationship (e.g., service provider to client or customer) with the entity using the provided services. Aspects of the image analysis approach discussed herein may be understood as potentially being implemented in such a networked or cloud-based scenario. However, it should also be understood that in other contexts or implementations all or part of the image analysis approach may be implemented on local processing systems to the image acquisition system, including on processing components of the image acquisition system itself, or on a local network accessible to the image acquisition system.

To facilitate explanation, particular examples of one suitable type of imaging system (e.g., a medical imaging system such as a mammography system) are described herein so as to provide a real-world context and a useful example for understanding the disclosed approach. As will be appreciated, the present approach may also be employed in conjunction with other imaging modalities and contexts, including various medical imaging modalities as well as security screening contexts, manufacturing quality review/control contexts, and so forth.

With this in mind and turning to FIG. 1, a simplified system figure is depicted providing a high level view of certain components and aspects of one example of a suitable imaging system or modality. In this example, a mammography imaging system 120 for use in accordance with the present approach is illustrated diagrammatically. As depicted, the imaging system 120 includes an X-ray source 124, an X-ray detector 126 and a compression assembly 128 that may be used to position the patient tissue and to generate signals representative of X-ray transmission through the tissue of interest. The mammography system 120 further includes a system controller 132, data acquisition and image-processing circuitry 136, an operator interface 138 and a display 140, some or all of which may be embodied as the mammography system 120.

The X-ray source 124 may, in certain implementations, include an X-ray tube (or other suitable X-ray generating mechanism) and a collimator configured to, in combination, generate and shape a beam of X-rays 142 when active. In a mammography embodiment, the X-ray detector 126 may be positioned proximate to and beneath the breast tissue of the patient during an examination, and thus may be incorporated as part of, or proximate to, the compression assembly 128. For example, the X-ray detector 126 may be disposed immediately or proximately beneath a bottom plate of compression assembly 128 such that the breast tissue does not rest directly on the detector 126 but on a plate or other compression support above the detector 126. In addition, an anti-scatter grid may be present between the detector 126 and the compression support.

In a mammography implementation, a compression assembly 128 may be employed to compress the breast tissue during image acquisition. In particular, the compression assembly 128 may be used to stabilize the imaged breast tissue during acquisition of the mammography images and to maintain uniformity of the tissue both during and between image acquisitions. In one embodiment, the compression assembly includes a lower plate 150, (such as a flat, inflexible plate) on which the breast tissue may rest, and an upper plate or paddle 152 which lowers onto the breast tissue to effect compression.

In the depicted implementation, the system controller 132 controls operation of the mammography imaging system 120. By way of example, the system controller 132 may control activation or operation of one or more of the X-ray source 124 (such as the activation timing, power, spectral distribution, and so forth), the detector 126 and data acquisition circuitry 136 (as discussed in greater detail below), and the compression assembly 128 if a motorized or automated compression mechanism is employed.

Typically, the data acquisition and image-processing circuitry 136 communicates with the X-ray detector 126 and receives data from the X-ray detector 126, such as a plurality of sampled analog signals or digitized signals resulting from exposure of the X-ray detector to X-rays. The data acquisition and image-processing circuitry 136 may convert the data to digital signals suitable for processing and/or may process sampled digital and/or analog signals to generate radiographic images of the breast tissue which may, in turn, be displayed on the display module 140 or printed if a printer is available.

An operator interface 138 can be used to input or adjust settings for the mammography imaging system 120 as well as for allowing operator activation and operation of the mammography imaging system 120. In the depicted embodiment, the operator interface 138 is connected to the system controller 132, image-processing circuitry 136, and the display 140.

In the depicted example, the data acquisition and image-processing circuitry 136 of the mammography system 120 is also in communication with a picture archiving and communications system (PACS) 158, which may in turn be coupled to one or more remote processing resources 156, such as an application or application server configured to implement an image quality analysis as discussed herein and executing in a cloud-based environment or on a remote network. Though FIG. 1 depicts a particular implementation in which a PACS system 158 is an intermediary between the mammography system 120 and the remote processing resources 156, in practice the mammography system 120 may be configured to communicate directly with the remote processing resources 156, without employing an intermediary such as the depicted PACS. Similarly, in further implementations, the application or routines corresponding to the image quality analysis described herein may be wholly or partly executed on the local processing circuitry 136 of the mammography system, though such a localized implementation may not receive certain benefits that a cloud-based implementation would, such as benefits related to stability, resource management, ease of updating, and so forth.

With the preceding in mind, the present approach may be employed in conjunction with an imaging system, such as that shown in FIG. 1 or otherwise, provided at a dedicated scanning site or at a mobile or remote site that might not typically have image analysis resources found at a dedicated facility. In one implementation, the present approach may include a complete schema with image compression, efficient upload to one or more image processing and analysis resources to the cloud (or other remote-networking environment), and detection of non-conformities in the images using analysis algorithms executing on an application server in the cloud or remote-networked environment (such as algorithms or analytics implemented as microservices on an application server in the cloud). Anomalies found in the images can be either caused by human error (such as when positioning the breast in a mammography context) or undesirable artifacts inadvertently generated by the scanner. By analyzing images for these non-conformities in real-time or near real-time, the present approach allows re-imaging to occur while the patient is still present in the exam room and prevents situations where patients have come back unnecessarily for additional imaging.

In one embodiment, the proposed approach implements different image analysis algorithms in a microservice-based architecture in the cloud (or other remote-networking environment) for detecting a set of specified non-conformities. This approach may benefit from software quality factors provided by the microservice-based architecture, such as improved flexibility and robustness.

Advantages of the present approach include, but are not limited to: (i) providing a systematic approach for assessing the image quality (such as in the context of mammography or other medical exams) in real-time; (ii) using a cloud- or network-based solution for quality control based on image analysis, and (iii) using a cloud- or network-based infrastructure that allows fast update and inclusion of new image analysis algorithms for handling other non-conformity issues in the specified imaging context, such as mammography.

To facilitate explanation, the following examples are provided in the context of a mammography imaging system so as to provide a real-world context and a useful example for understanding the disclosed approach. However, as noted above, the present approach may also be employed in conjunction with other imaging modalities and contexts, including various medical imaging modalities as well as security screening contexts, manufacturing quality review/control contexts, and so forth.

With than in mind, in one example mammography image quality is assessed in real-time, such as while the patient is still present at the imaging site and, in one implementation, while the patient is still in position for re-imaging. In particular the approach helps the technician to more quickly determine if an acquired image has non-conformities of certain specified types and, if present, to repeat all or part of the exam accordingly. In addition, this approach can help avoid patients having to come back for re-imaging when an image is unsuitable. Consequently, this approach has potential to reduce both exam and diagnostics costs, and false positives and false negatives during the diagnostics.

The types of non-conformities addressed may vary depending on the imaging context, though certain non-conformities may be common to many or all imaging contexts. By way of example, in a mammography context, non-conformities that may be handled in accordance with the present approach include, but are not limited to: 1) bad pixels in the image, 2) line artifacts in the image, 3) scan parts being included in the image, 4) absence of breast/chest angle in a medio-lateral oblique (MLO) view, 5) misalignment of pectoral muscle and nipple in a MLO view, 6) non-centered nipple in a cranial- or center-caudal (CC) view, and 7) absence of pectoral muscle in a CC view. By some estimates, in a mammography context these seven types of non-conformities may represent 60% or more of mammography non-conformity image issues.

Figure 2:
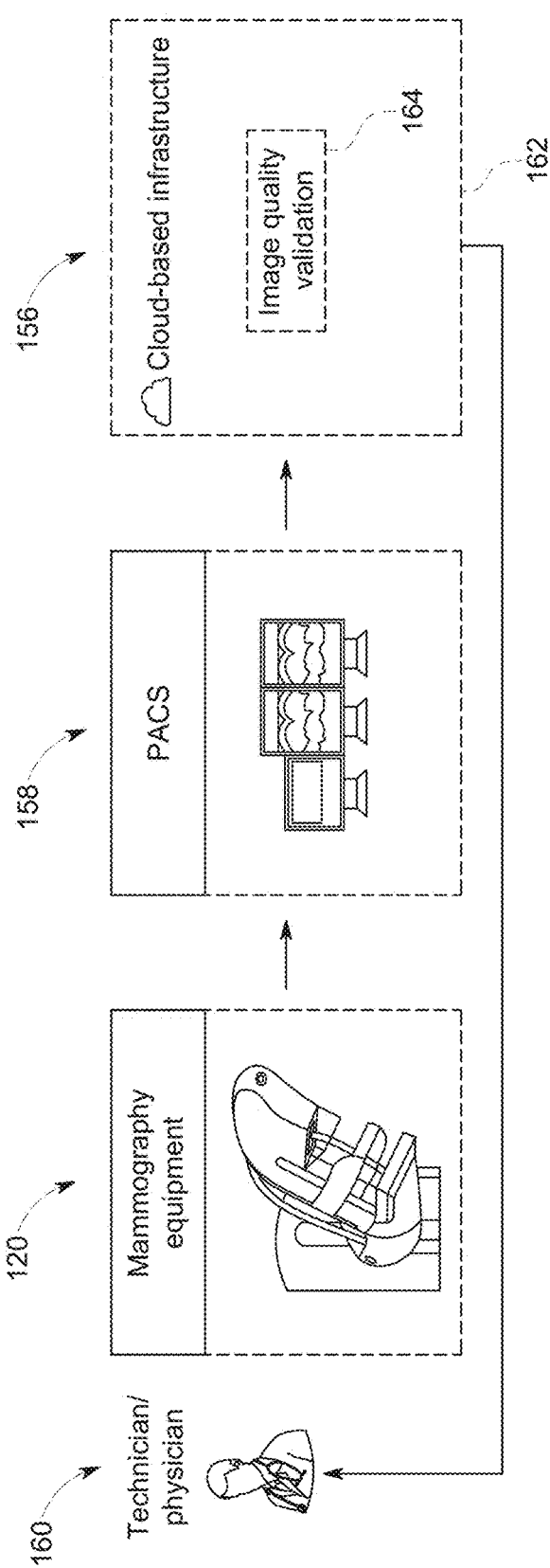
FIG. 2 depicts a process flow of an algorithmically-driven image quality assessment using remote processing resources, in accordance with aspects of the present disclosure.

Turning to FIG. 2, a high-level view of a process flow for the present approach is shown. In this example, a technician 160 performs a mammography exam procedure (using the mammography imaging system 120) and the resulting images, either automatically or in response to a prompt from the user, are transmitted to a PACS 158. In this implementation, when the images are uploaded to the PACS 158, they are also automatically sent to a remote processing resource 156, such as a cloud-based application infrastructure 162 (e.g., cloud-based processors, databases, memories, and so forth that may implement one or more application servers or other processing aspects). In this example, processing components of the cloud-based infrastructure 162 execute one or more image quality validation routines 164 implemented as services or microservices as discussed herein. For instance, the image quality validation routines 164 executed at the remote processing resources 156 may be stored and executed wholly or partially in parallel when an image is received for analysis so as to provide a result in real-time or near real-time to the technician 160. By way of example, the feedback provided to the technician 160 from the remote processing resources may be via a web interface or a special-purpose application interface (i.e., an "app"). Due to the result being generated in substantially real-time, the patient will still be present in the examination setting (i.e., at the imager) and available for re-imaging if the result indicated non-conformities in the uploaded images. In one embodiment, the feedback provided to the technician 160 may detail or otherwise specify the non-conformities identified in the uploaded images so the technician 160 can address the non-conformities in the subsequent images.

Figure 3:
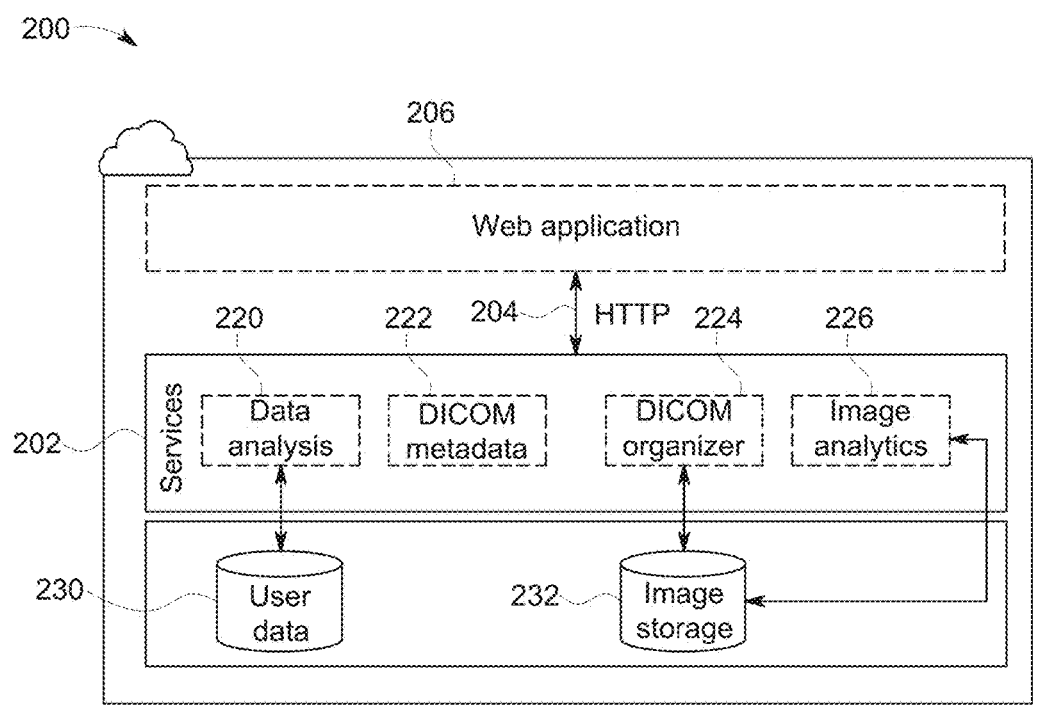
FIG. 3 depicts an implementation of a cloud-based architecture for providing image analysis services, in accordance with aspects of the present disclosure.

Turning to FIG. 3, an implementation of one example of a cloud-based architecture 200 is depicted. In one such example, the architecture 200 (cloud-based or otherwise) provides a set of services 202 that are equipment agnostic (i.e., work directly on the images), each with a well-defined purpose, and that are accessible via a hypertext transfer protocol (HTTP) resource application programming interface (API) 204. In this manner, it is possible to easily integrate the provided services 202 with any application 206 and to update the architecture 200 to modify existing services or add new services 202.

In one such implementation, the image quality validation discussed herein is provided via a microservice-based architecture in which the respective processes communicate over a network to provide the image quality validation service, using protocols that are indifferent to the particular hardware or technology implementation (i.e., which can be run on different platforms), such as HTTP. Such microservice-based architectures are typically characterized by the small or fine granularity of the services 202 and/or the lightweight nature of the protocols employed. In one implementation, the microservice-based architecture is implemented on an open-source cloud computing platform.

With respect to the services 202 themselves, in the medical imaging example shown in FIG. 3 the services include at least: a data analysis service 220, a DICOM (i.e., the digital imaging and communication in medicine standard covering, handling, storage, and transmission of medical images)) metadata service 222, a DICOM organizer service 224, and an image analytics service 226.

The data analysis service 220 comprises processor-executable routines (i.e., a software module) that, when executed, cause or facilitate the updating, storing and/or querying of the images to be analyzed. In one implementation the data analysis services 220 provide means to interface with the user data 230 (which may be stored in a relational database system (RDS) or other database context) and the image storage 232, which may be provided as a secure and scalable object storage service. In the present example, the image storage 232 is used to store mammography images, while the database 230 is used to store and manage user data, types of non-conformities in the images after being analyzed, equipment data, and so forth.

The DICOM metadata service 222 comprises processor-executable routines (i.e., a software module) that, when executed implement the image analysis algorithms discussed herein. In one implementation the DICOM metadata service 222 extracts image metadata, such as the respective technician's identifier, equipment information (e.g., the imaging system (or other equipment) model, manufacturer, unique identifier (e.g., serial number), and so forth), date and/or time, examination sequence number or identifier, hospital or facility (or other location information such as GPS coordinates), and so forth.

The DICOM organizer service 224 in the present example comprises processor-executable routines (i.e., a software module) that, when executed are responsible for the organization of images in the storage hierarchy (e.g., directories or folders in a storage space), typically using the original image metadata. By way of example, in one implementation, the first level of organization is an identifier of the technician who performed the exam, which may be used to limit access to the images such that each technician only has access to his or her exams. Other levels of organization based on the image metadata may be based on the date and time metadata and/or on the examination identifier or sequence number.

The image analytics service 226 comprises processor-executable routines (i.e., a software module) that, when executed implement the image analysis algorithms discussed herein. In one implementation, the image analysis algorithms are implemented as small, self-contained services and executed in parallel so as to benefit from the cloud structure and to deliver prompt feedback of non-conformities in a given exam. In a present mammography example, the non-conformities identified by the image analytics service, include, but are not limited to: 1) bad pixels in the image, 2) presence of line artifacts in the image, 3) presence of scan parts in the image, 4) absence of breast/chest angle in medio-lateral oblique (MLO) view, 5) misalignment of pectoral muscle and nipple in MLO view, 6) non-centered nipple in cranial- or center-caudal (CC) view, 7) absence of pectoral muscle in CC view.

In addition, as shown in the depicted example, the image analysis services communicate with a web application 206. In one such embodiment, the web application corresponds to an application front-end with which a user (e.g., technician) interacts. In this example the web application 206 connects with the services 202 in a cloud-based (or other network-based) implementation through HTTP requests 204 and using a defined API. Example of interfaces for a suitable web application are discussed below after a discussion of image analytics implemented using certain contemplated approaches.

Figure 4:
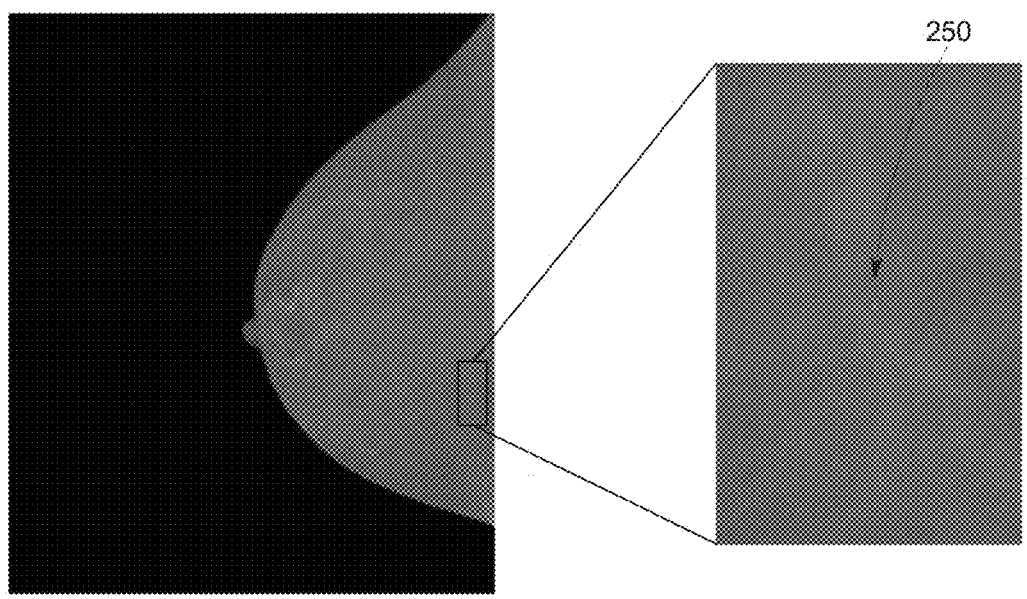
FIG. 4 depicts a side view of an imaged breast and a blown-up region of the image illustrating a bad pixel, in accordance with aspects of the present disclosure.

As noted above, and with respect to the image analysis process, one contemplated image analysis service may be directed to identifying bad pixels. A bad pixel in an imaging context, such as the present mammography example, may be characterized as a pixel that has a relatively high grey value (i.e., intensity) relative its neighbors. That is, the bad pixel typically has a high gray value or intensity and is surrounded by a group of pixels having lower values. An example of a bad pixel 250 is shown in FIG. 4, where a side view of an imaged breast is shown with an imaged region blown up for easier viewing. Within the blown up region, a bad pixel 250 is depicted as having a high intensity or response relative to its neighbors.

Figure 5:
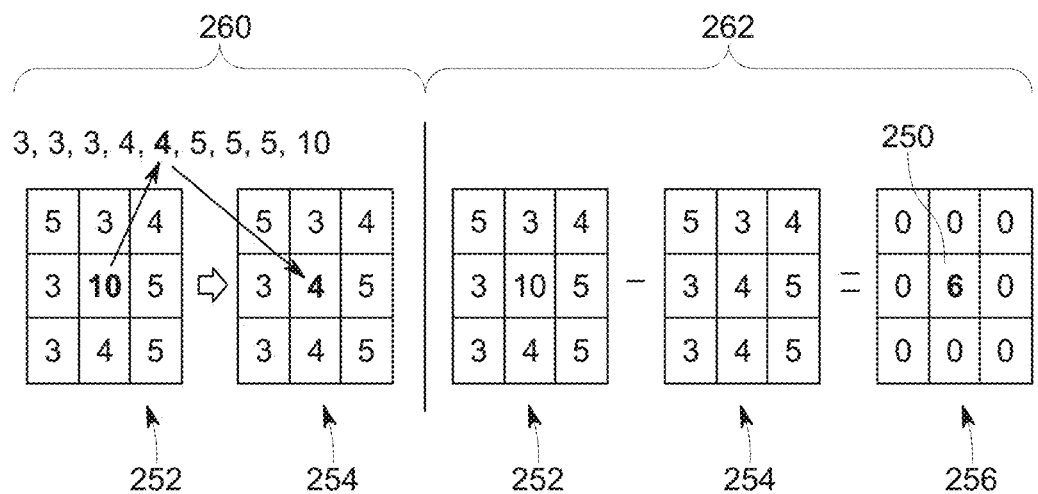
FIG. 5 depicts a bad pixel detection process flow, in accordance with aspects of the present disclosure.

In the present context, one service or microservice that may be characterized as an image analytic service 226 executes a bad pixel detection algorithm (i.e., a bad pixel detection service or microservice). In one example, the executed algorithm detects bad pixels 250 based on the difference between the original image and the same image filtered using a median filter. An example of this approach is shown in FIG. 5 where a 3×3 neighborhood of pixel having intensity values displayed as whole numbers is shown. In this example, the array 252 of original image intensity values is median filtered in a first step 260 to yield a corresponding median-filtered array 254. In a second step 262, the values in the median-filtered array or image 254 is subtracted from the corresponding original image intensity values of array 252 to yield a difference image or array 256. Based on a threshold comparison, the values within the difference image or array 256 may be compared to a numeric threshold and, if exceeding the threshold, deemed to correspond to a bad pixel 250.

Figure 6:
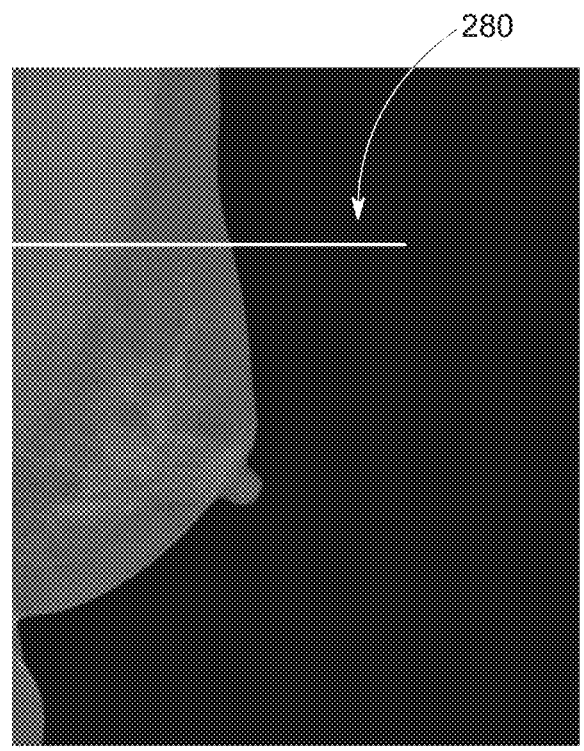
FIG. 6 depicts a side view of an imaged breast illustrating a bad line, in accordance with aspects of the present disclosure.

With respect to other aspects of the image analysis process, another contemplated image analysis service may be directed to detecting bad lines. A bad line in an imaging context, such as the present mammography context, may be characterized as a single line that has a relatively high grey value (i.e., intensity) relative the proximate or adjacent lines. That is, the bad line typically has a high gray value or intensity and is surrounded by a group of pixels having lower values. An example of a bad line 280 is shown in FIG. 6, where a side view of an imaged breast is shown.

In the present context, one service or microservice that may be characterized as an image analytic service 226 executes a bad line detection algorithm (i.e., a bad line detection service or microservice). In one example, the executed algorithm detects bad line 280 based on a Hough transform for line detection, which uses a Canny contour extraction combined with a voting schema to find the most likely lines given a set of contour points. A voting threshold defines strong candidates and finds bad lines in the images. The bad line 280 may be visually indicated or enhanced (such as by color enhancement) for review by the technician or the algorithm may simply provide an indication of non-conformities in the form of one or more bad lines 280 being present in the image. As may be appreciated, identification of bad pixels or bad lines, to the extent such artifacts are indicative of equipment failures or issues, may serve as prompts for the automatic or manual generation of a service call.

Figure 7:
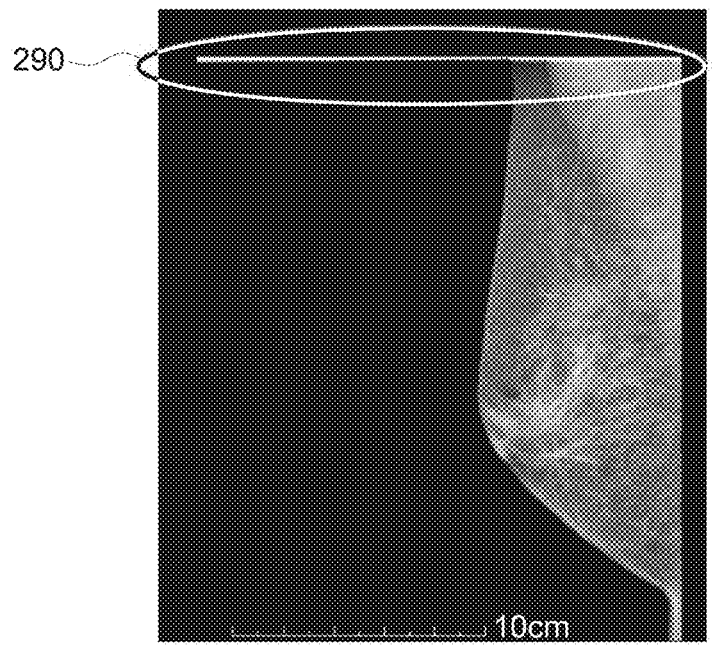
FIG. 7 depicts a side view of an imaged breast illustrating inadvertent imaging of a component of the imaging system, in accordance with aspects of the present disclosure.

In a similar context, another contemplated image analysis service may be directed to detecting artifacts caused by the components of the imager system that are inadvertently imaged or otherwise affect the images. By way of example, a collimator, which typically is a radio-opaque structure used to shape or limit the X-ray emission, may inadvertently intrude on regions of the image. For example, such an effect, when present, happens when part of an auxiliary component of the scanning process (such as the collimator) appears in the image. Such effects typically manifest as a bright (i.e., high intensity), generally straight artifact at the image borders. An example of an imaged collimator (i.e., artifact 290) is shown in FIG. 7, where a side view of an imaged breast is shown.

In the present context, one service or microservice that may be characterized as an image analytic service 226 executes a collimator (or other imager component) detection algorithm (i.e., a hardware detection service or microservice). In one example, the executed algorithm detects hardware-related artifacts 290 (such as collimator artifacts) based on a Hough transform as discussed above. In this implementation, the Hough transform is used to find straight lines close to the border of the image, which indicates the presence of undesired scan parts in the image.

Figure 8:
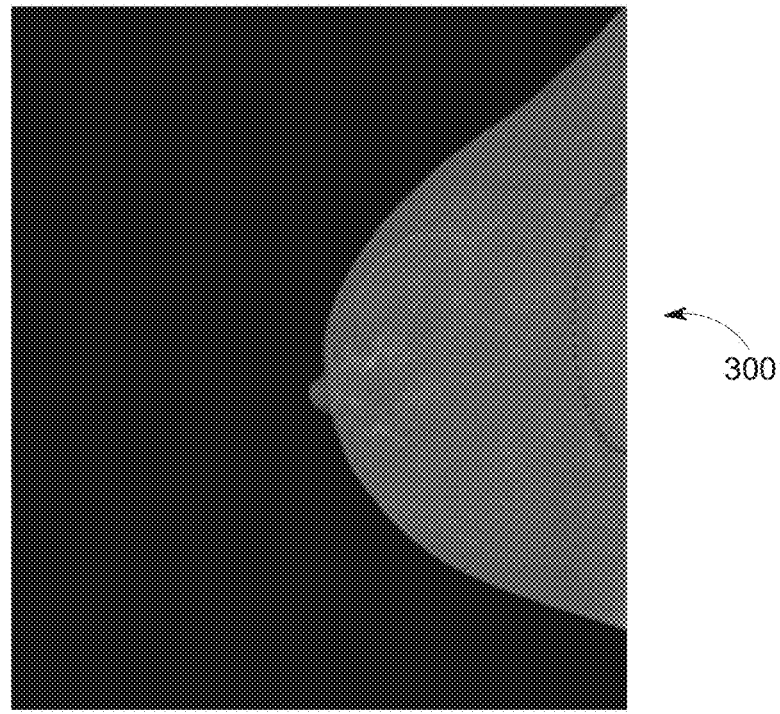
FIG. 8 depicts a cranial- or center-caudal (CC) view of an imaged breast illustrating detection of muscle in the image, in accordance with aspects of the present disclosure.

In a further aspect, another contemplated image analysis service may be directed to detecting musculature in a cranial- or center-caudal (CC) view (i.e., a top-down view or view from above). As shown in FIG. 8, in a CC view in a mammography context the pectoral muscle 300 should be present and appear as a bright semi-elliptical structure (encircled in FIG. 8 by a dashed line) touching the border at the inner part of the breast. The muscle should be visible, when possible, in the mammography images. If it is not visible the fat between the glands and the muscle must be visible. If none is visible the exam must be repeated, i.e., the images re-acquired.

In the present context, one service or microservice that may be characterized as an image analytic service 226 executes a muscle detection (e.g., a pectoral muscle detection) algorithm (i.e., a muscle detection service or microservice). In one example, the executed algorithm detects the pectoral muscle in CC images using a voting schema for fitting an ellipsis at a point of interest inside the breast. In particular, when visible in a CC view, the pectoral muscle 300 is usually a bright area that follows roughly the shape of a semi ellipsis in the image border, as shown in FIG. 8. The contemplated muscle detection algorithm iteratively tries different combinations of ellipsis centers and ratios to find the ellipsis that fits the best the gradient magnitude image derived from the original image. With this approach, the contour of the muscle is found by adding a semi ellipsis geometric constraint.

Figure 9:
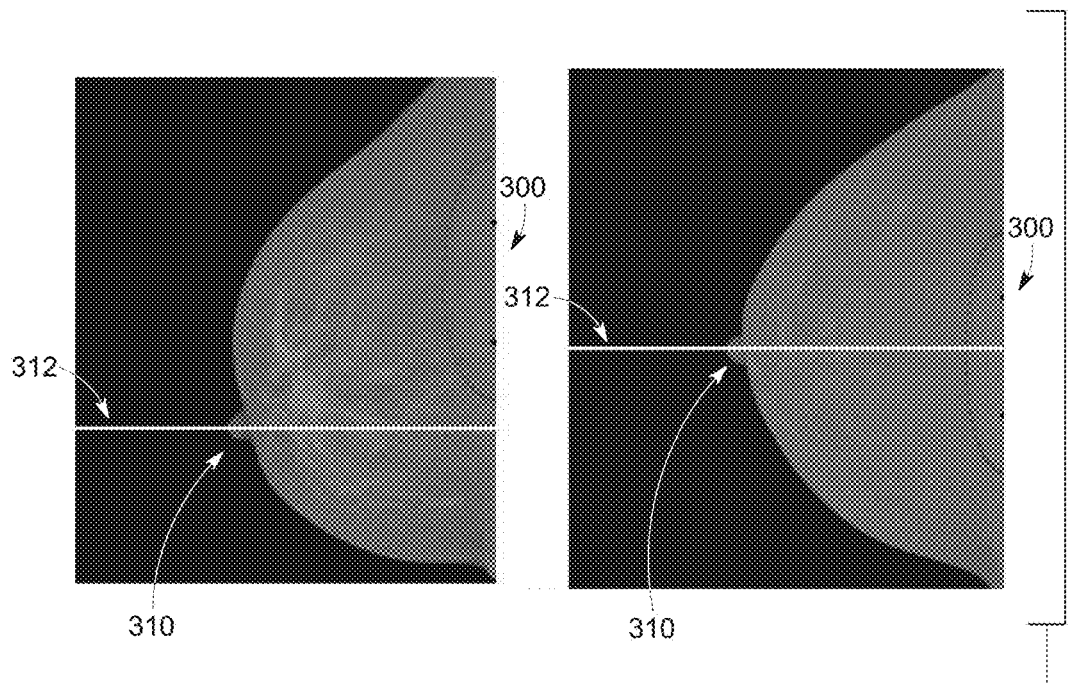
FIG. 9 depicts a cranial- or center-caudal (CC) views of an imaged breast illustrating detection of nipple centering in the image, in accordance with aspects of the present disclosure.

In another aspect, a contemplated image analysis service in a mammography context may be directed to detecting whether the nipple is properly positioned and oriented in a given image. For example, as shown in FIG. 9, in such a mammography context in a CC view the nipple 310 appears as a point at the breast border where the skin is a bit wider and located usually at the most distant point with respect to the pectoral muscle 300. The nipple's extension outward should be centered in relation to the breast, and ultimately to the pectoral muscle 300.

With this in mind, in the present context, one service or microservice that may be characterized as an image analytic service 226 executes a nipple position and orientation algorithm (i.e., a centered nipple evaluation service or microservice). In one example, the executed algorithm uses a pectoral muscle location (as may be determined by the service described above) and detects the nipple 310 as the more distant point from the breast surface with respect to the pectoral muscle 300. A determination may then be algorithmically made as to whether the nipple 310 is centered with respect to the pectoral muscle 300. For example, such a determination may be made by determining if the y-coordinate value of the nipple position (indicated by lines 312 in FIG. 9) is between a range of y-coordinate values centered inside the pectoral muscle 300. If it falls inside the range, the nipple 310 is centered, otherwise it is not. Examples of a non-centered nipple 310 (FIG. 9, leftmost image) and a centered nipple 310 (FIG. 9, rightmost figure) are provided by way of illustration.

In another aspect, a contemplated image analysis service in a mammography context may be directed to determining that the breast/chest angle is visible in a mediolateral-oblique (MLO) view, i.e., an oblique or angled view, conventionally a view from the side and at an angle. In an MLO view context, the angle of the breast relative to the abdomen should be visible. If this angle is not visible in the image, the exam must be repeated, i.e., the images re-acquired.

Figure 10:
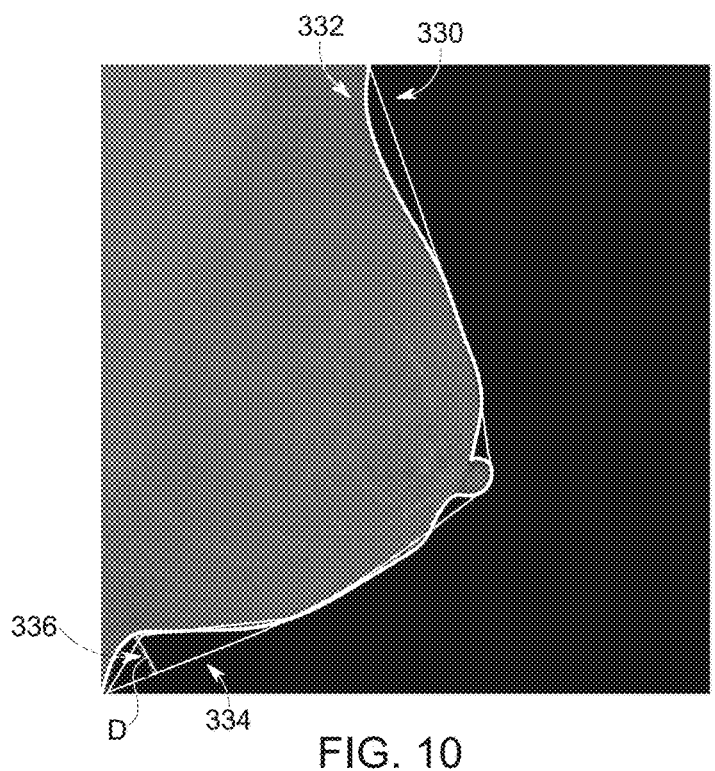
FIG. 10 depicts a mediolateral-oblique (MLO) view of an imaged breast illustrating breast/chest angle detection in the image, in accordance with aspects of the present disclosure.

In the present context, and turning to FIG. 10, one service or microservice that may be characterized as an image analytic service 226 executes an MLO angle detection algorithm (i.e., a service or microservice that detects whether a breast/chest angle is discernible in MLO images). In one example, the executed algorithm detects the angle between the breast and the chest using the convex hull (line 330) and the breast border (boundary line 332). The angle 334 is defined as the point in the bottom part of the breast that has a maximum distance (distance line 336) between the breast border 332 and convex hull line 330. If this distance 336 is greater than a specified threshold, the algorithm deems the angle 334 to be visible. If the distance 336 is below the threshold or not determinable, the algorithm deems the angle 334 not visible.

In a further aspect, a contemplated image analysis service in a mammography context may be directed to determining if, in the MLO view the nipple latitude intersects the pectoral muscle. If the nipple latitude intersects the pectoral muscle, this helps to ensure that the fibro-glandular tissue is present in the image. Conversely, when the nipple latitude does not intersect the pectoral muscle, alignment error is indicated and the exam must be repeated, i.e., the images re-acquired.

By way of example, in the present context one service or microservice that may be characterized as an image analytic service 226 executes an MLO nipple/muscle alignment algorithm (i.e., a service or microservice that determines whether the nipple latitude intersects the pectoral muscle in MLO images). In one example, the executed algorithm assesses the alignment between the nipple and pectoral muscle in an MLO view by performing three alignment assessment steps. In the first step, the pectoral muscle is detected in the MLO view.

Figure 11:
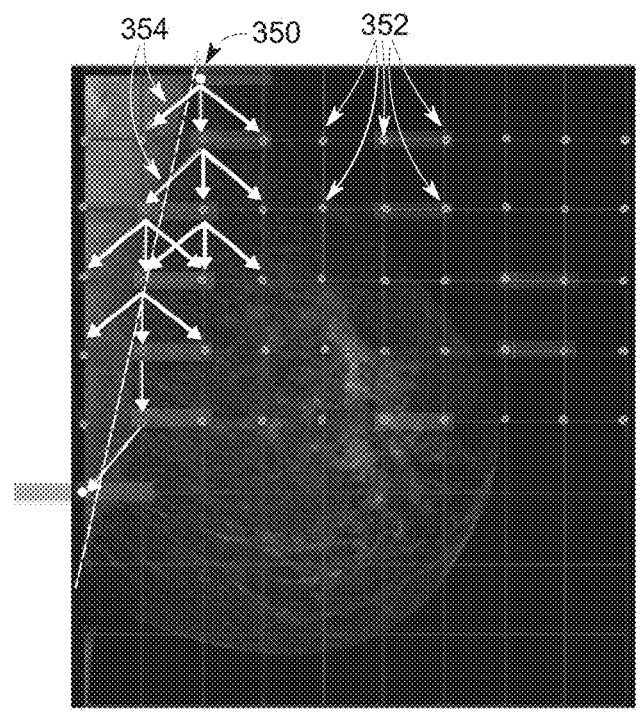
FIG. 11 depicts a mediolateral-oblique (MLO) view of an imaged breast illustrating pectoral muscle detection in the image, in accordance with aspects of the present disclosure.
Figure 12:
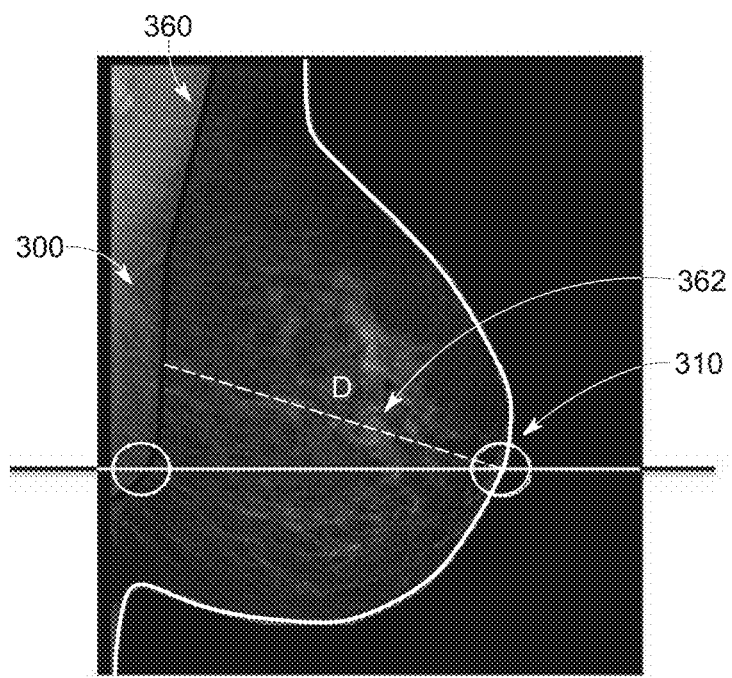
FIG. 12 depicts a mediolateral-oblique (MLO) view of an imaged breast illustrating detection of nipple muscle alignment in the image, in accordance with aspects of the present disclosure.

With respect to detecting the pectoral muscle in the MLO view, in one example the algorithm executed by the service detects the pectoral muscle by performing a series of pectoral muscle detection steps, shown graphically in FIG. 11, which may include, but are not limited to: (1) finding a starting point 350 as the position with the highest gradient value in the breast at the top border, (2) creating a directed weighted graph using a similarity measure between the nodes (illustrated as circles 352) as the weights in the graph, (3) considering the shortest paths between the starting point 350 and each of the set of key points inside the breast at the left/right border (denoted by arrowed lines 354), and (4) selecting the path with the minimum final score (dark shaded path arrows) as the border 360 (FIG. 12) of the pectoral muscle 300. The shortest path roughly follows the (usually discontinuous) gradient line that bounds the pectoral muscle 300 with respect to the fat inside the breast, delimiting an area corresponding to the pectoral muscle 300.

In a second alignment assessment step (which may actually be performed in parallel with or prior to the pectoral muscle detection), the nipple 310 is detected in the MLO view. In one implementation, shown in FIG. 12, the nipple 310 is detected as the most distant point (as illustrated by Distance line D) with respect to the pectoral muscle 300. In the third step the alignment (alignment line 362) between the nipple 310 and pectoral muscle 300 is verified, such as based on the height of the nipple.

Figure 13:
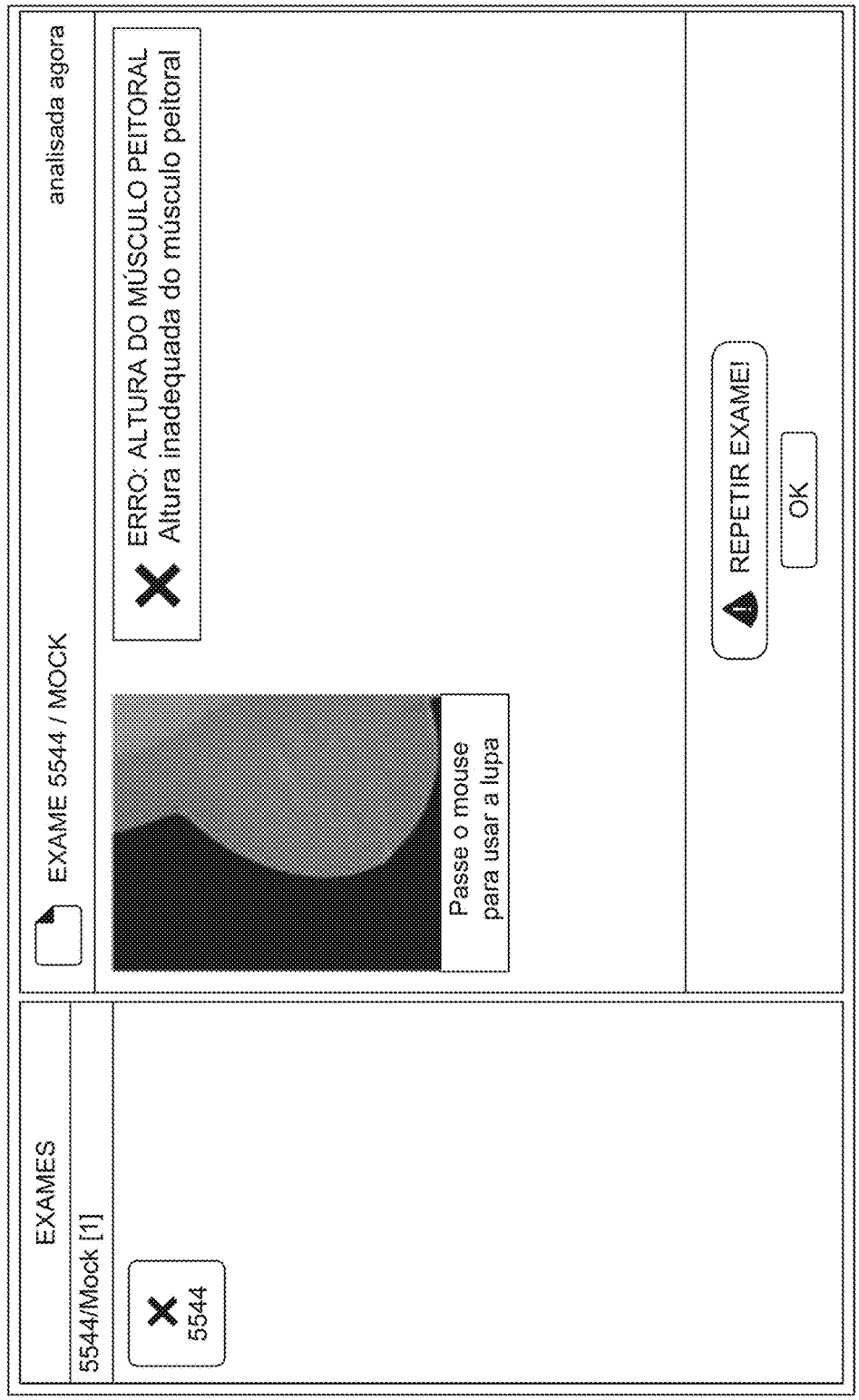
FIG. 13 depicts a screen shot of an application for displaying non-conformity results to a technician, in accordance with aspects of the present disclosure.
Figure 14:
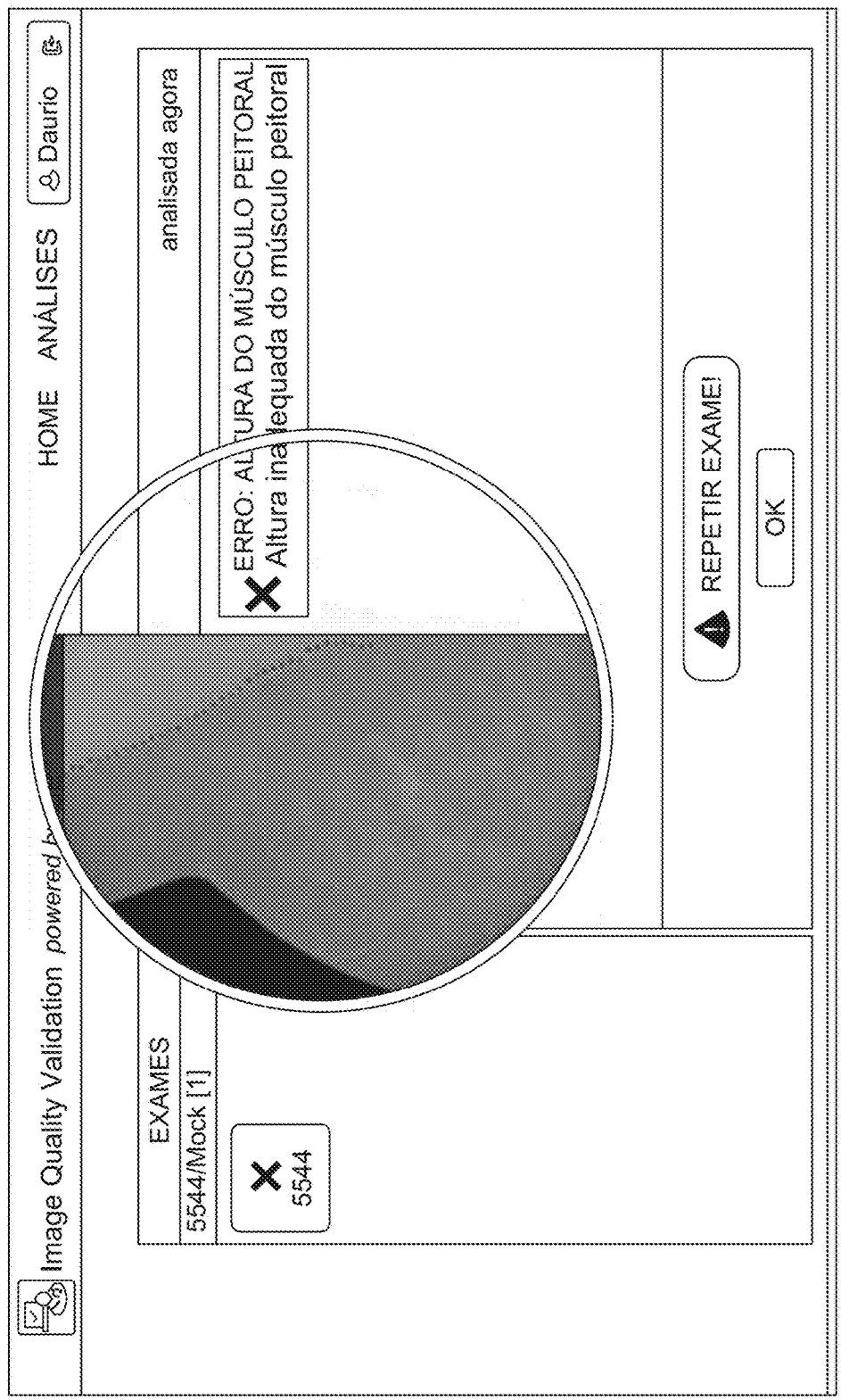
FIG. 14 illustrates a visual enhancement to the screen shown in FIG. 13 in response to a user input, in accordance with aspects of the present disclosure.
Figure 15:
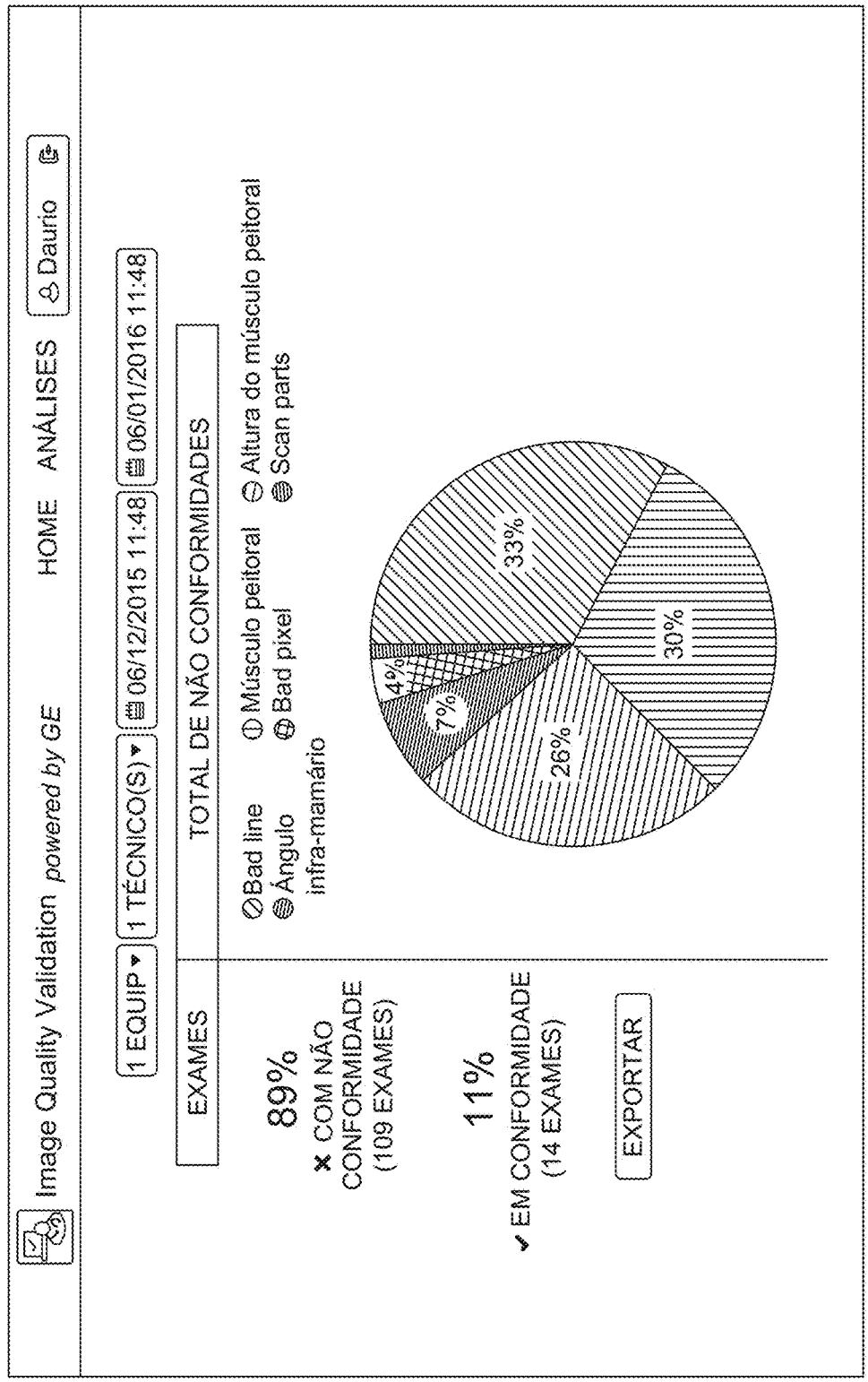
FIG. 15 illustrates an analytics screen of an image analysis application form which a user may sort results based on useful parameters, in accordance with aspects of the present disclosure.

While the preceding relates to the image analytics services and algorithms employed, as noted previously the interface component of the outputs of these analytics to the technician may take the form of a web application 206 (FIG. 3). In one implementation, the web application may provide various views, such as a technician view (where the technician can visualize the analyzed images and understand the associated non-conformities), an example of which is shown in FIGS. 13 and 14, and/or a physician view (where visualization of the data analyses and/or generation of reports is provided), as shown in FIG. 15. Reports generated in a physician's view may be used to better understand the number and types of non-conformities observed in the images based on or broken down by: (1) technicians, (2) equipment, and (3) time frame.

Turning to FIGS. 13, and 14, these figures depict screenshots that may be displayed to a technician. The screenshots in this example display or more images that have been analyzed and the non-conformities that were detected. Non-conformities may be highlighted or pointed out in the relevant images using visual cues or highlighting and/or may be identified by a suitable error message. In one example, the technicians can navigate through the images and zoom in using the mouse (as shown in FIG. 14) to see more details about the non-conformities. As previously noted, the results provided to the technician (such as shown in FIGS. 13 and 14) may be generated in the cloud or other networked location and returned to the technician in real-time or near real-time, such as while the patient is still in the imaging position corresponding to the results depicted in the web application screen. In this manner, the results may be provided in a time frame that allows re-imaging for a given pose where the image was determined to be non-conforming.

Conversely, FIG. 15 depicts a data analysis screen where a clinician or administrator can obtain more detail about a number of analyzed images (such as images acquired by a given technician, using a given imaging system, and/or over a given time frame) and the types of non-conformities observed. Such data analyses can then be used for making determinations related to: scheduling suitable training for a given technician prone to certain types of errors and/or scheduling maintenance or servicing for an imaging system exhibiting certain hardware related errors (e.g., bad pixels, bad lines, and so forth).

Technical effects of the invention include providing image quality feedback to personnel (e.g., a technician) acquiring non-invasive images in real-time or near real-time, such as in less than 5 seconds, 10 seconds, 20 seconds, 30 seconds, 1 minute, 2 minutes, or 5 minutes of the image being acquired. By way of example, the proposed approach may automatically assess the quality of mammography images in real-time by evaluating the images for the presence or absence of non-conformities using processor-implemented, rule-based algorithms running partly or completely in parallel to one another. The proposed approach improves the image analysis pipeline by efficiently providing notification of and/or discarding low-quality or clinically unsuitable images or exams after they are taken, such as in within seconds or minutes. Such notification may, in certain implementations occur while patient or object is still present and/or positioned for a follow-up imaging attempt. In accordance with the present disclosure the image analysis approach may be implemented as a cloud-based image analysis instance (or other remote or networked implementation) so as to provide real-time or near real-time feedback to personnel tasked with acquiring the image data regardless of geographic location.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An imaging system, comprising:
an X-ray source configured to emit X-rays;
a radiation detector configured to generate signals in response to the emitted X-rays incident on a surface of the radiation detector;
data acquisition circuitry configured to use the signals to generate one or more mammographic images that are transmitted directly or indirectly to a remote processing resource configured to execute a plurality of services which each evaluate the one or more images for a different type of non-conformity; and
an operator interface and display configured to execute an application that notifies a technician in real-time or near real-time to determine if a plurality of non-conformities of the one or more mammographic images identified by the remote processing resource includes a predetermined type of non-conformity, wherein the plurality of non-conformities include one or more of: absence of a breast/chest angle in an MLO view, wherein the MLO is a mediolateral-oblique;
misalignment of a nipple and pectoral muscle in an MLO view, wherein the MLO is a mediolateral-oblique;
non-centered nipple in a CC view, wherein the CC is a center-caudal;
and absence of pectoral muscle in the CC view, wherein the CC is a center-caudal.

2. The imaging system of claim 1, wherein the imaging system comprises a mammography imaging system.

3. The imaging system of claim 1, wherein the remote processing resource comprises a cloud-based resource.

4. The imaging system of claim 1, wherein the one or more images are transmitted to the remote processing resource via a picture archiving and communication system intermediary.

5. The imaging system of claim 1, wherein the identified non-conformities are displayed in less than 1 minute from the time a respective image is acquired.

6. The imaging system of claim 1, wherein the identified non-conformities are displayed while a patient is still at a site of the imaging system.

7. An image analysis architecture, comprising:
an X-ray source configured to emit X-rays;
a radiation detector configured to generate signals in response to the emitted X-rays incident on a surface of the radiation detector;
a data acquisition circuitry configured to use the signals to generate one or more mammographic image files;
an application interface configured to be displayed at the site of an imaging system and to facilitate the transfer of die one or more mammographic image files to a remote processing resource; and
a plurality of services executable on the remote processing resource, wherein at least a portion of the services are configured to execute in parallel and wherein each service is configured to analyze the one or more mammographic image files for a respective type from a plurality of non-conformities and to provide a notification to a technician in real-time or near real-time via the application interface to determine based on a threshold if a pre-determined type of non-conformity is identified, wherein the plurality of non-conformities include one or more of:
absence of a breast/chest angle in an MLO view, wherein the MLO is a mediolateral-oblique;
misalignment of a nipple and pectoral muscle in an MLO view, wherein the MLO is a mediolateral-oblique;
non-centered nipple in a CC view, wherein the CC is a center-caudal;
and absence of pectoral muscle in the CC view, wherein the CC is a center-caudal.

8. The image analysis architecture of claim 7, wherein the remote processing resource comprises a cloud-based resource.

9. The image analysis architecture of claim 8, wherein the cloud-based resource comprises one or more application servers.

10. The image analysis architecture of claim 7, wherein the plurality of non-conformities include one or more of: bad pixels, line artifacts, or components of the imaging system shown in the image.

11. A method for remotely assessing image quality, comprising:
   emitting X-rays using an X-ray source;
   generating signals using a radiation detector in response to the emitted X-rays incident on a surface of the radiation detector;
   receiving an image of a patient or object using the signals generated at a site of an imaging system, wherein the image comprises mammographic images;
   processing the image using a plurality of image quality analysis services, at least a portion of which execute in parallel, wherein the image quality service analytics are executed on a network-based architecture physical remote form the site of the imaging system;
   transmitting one or more notifications of a plurality of non-conformities identified by the image quality analysis services to a technician in the site of the imaging system in less than a minute from the time the image was acquired to determine if the plurality of identified nonconformities includes a pre-determined type of non-conformity, wherein the plurality of nonconformities include one or more of:
   absence of a breast/chest angle in an MLQ view, wherein the MLO is a mediolateral-oblique;
      misalignment of a nipple and pectoral muscle in an MLO view, wherein the MLO is a mediolateral-oblique;
      non-centered nipple in a CC view, wherein the CC is a center-caudal;
      and absence of pectoral muscle in the CC view, wherein the CC is a center-caudal.

12. The method of claim 11, wherein the site is a mobile site presently occupied by a portable imaging system.

13. The method of claim 11, wherein the network-based architecture comprises a cloud-based architecture.

14. The method of claim 11, wherein the plurality of non-conformities include one or more of: bad pixels, line artifacts, or components of the imaging system shown in the image.

15. The method of claim 11, wherein the plurality of non-conformities relate to clinical standards for the position and/or orientation of a body part being imaged.

* * * * *